United States Patent [19]
Ben-Haim

[11] Patent Number: 5,954,665
[45] Date of Patent: Sep. 21, 1999

[54] CARDIAC ABLATION CATHETER USING CORRELATION MEASURE

[75] Inventor: Shlomo Ben-Haim, Haife, Israel

[73] Assignee: Biosense, Inc., New Brunswick, N.J.

[21] Appl. No.: 08/956,687

[22] Filed: Oct. 23, 1997

Related U.S. Application Data

[63] Continuation-in-part of application No. 08/476,200, Jun. 7, 1995, Pat. No. 5,718,241.
[51] Int. Cl.$^6$ .............................. A61B 5/04; A61B 5/0402
[52] U.S. Cl. .......................... 600/515; 600/518; 607/122
[58] Field of Search ............................... 607/6, 122, 125, 607/101; 600/515, 518

[56] References Cited

U.S. PATENT DOCUMENTS

| | | |
|---|---|---|
| 4,173,228 | 11/1979 | Van Steenwyk et al. . |
| 4,304,239 | 12/1981 | Perlin . |
| 4,431,005 | 2/1984 | McCormick . |
| 4,444,195 | 4/1984 | Gold . |
| 4,499,493 | 2/1985 | Nishimura . |
| 4,522,212 | 6/1985 | Gelinas et al. . |
| 4,573,473 | 3/1986 | Hess . |
| 4,613,866 | 9/1986 | Blood . |
| 4,628,937 | 12/1986 | Hess et al. . |
| 4,649,924 | 3/1987 | Taccardi . |
| 4,697,595 | 10/1987 | Breyer et al. . |
| 4,699,147 | 10/1987 | Chilson et al. . |
| 4,777,955 | 10/1988 | Brayton et al. . |
| 4,812,976 | 3/1989 | Lundy . |
| 4,821,731 | 4/1989 | Martinelli et al. . |
| 4,899,750 | 2/1990 | Ekwall . |
| 4,922,912 | 5/1990 | Watanabe . |
| 4,940,064 | 7/1990 | Desai . |
| 4,945,305 | 7/1990 | Blood . |
| 5,000,190 | 3/1991 | Petre . |
| 5,012,814 | 5/1991 | Mills et al. . |
| 5,025,786 | 6/1991 | Siegel . |

(List continued on next page.)

FOREIGN PATENT DOCUMENTS

| | | |
|---|---|---|
| 0499491 | 8/1992 | European Pat. Off. . |
| 9406349 | 3/1994 | WIPO . |
| WO 96/05768 | 2/1996 | WIPO . |

OTHER PUBLICATIONS

Josephson et al., Role of Catheter Mapping in the Preoperative Evaluation of Ventricular Tachycardia, *The American Journal of Cardiology*, vol. 40, pp. 207–220, Jan. 1982.

Josephson et al., Comparison of Endocardial Catheter Mapping with Intraoperative Mapping of Ventricular Tachycardia, *Circulation*, vol. 61, No. 2, pp. 395–404, 1980.

Josephson et al., Ventricular Activation During Ventricular Endocardial Pacing—II: Role of Pace–Mapping to Localize Origin of Ventricular Tachycardia *The American Journal of Cardiology*, vol. 30, 50, pp. 11–22, Jul. 1982.

Witnowski et al., An Automated Simultaneous Transmural Cardiac Mapping System, *American Journal of Physiology* vol. 247, pp. H661–H668, 1984.

Fann et al., Endocardial Activation mapping and Endocardial Pace–Mapping Using a Balloon Apparatus, *American Journal of Cardiology* vol. 55, pp. 1076–1083, Apr. 1, 1985.

(List continued on next page.)

*Primary Examiner*—William E. Kamm
*Assistant Examiner*—Carl H. Layno
*Attorney, Agent, or Firm*—Cowan, Liebowitz & Latman; William H. Dippert

[57] ABSTRACT

Apparatus for endocardiac therapy, including an elongate probe for insertion into the heart of a subject, the probe having distal and proximal ends. The probe includes an ablation device near the distal end of the probe for ablating heart tissue and at least two sensing electrodes, for sensing activation signals in the heart tissue adjacent to the ablation device. Signal analyzer circuitry receives and correlates the activation signals. Preferably, the probe includes a position sensor adjacent to the ablation device, which generates signals responsive to the position of the probe with respect to an external frame of reference.

40 Claims, 3 Drawing Sheets

U.S. PATENT DOCUMENTS

| | | |
|---|---|---|
| 5,041,973 | 8/1991 | Lebron et al. . |
| 5,042,486 | 8/1991 | Pfeiler et al. . |
| 5,054,492 | 10/1991 | Scribner . |
| 5,054,496 | 10/1991 | Wen et al. . |
| 5,056,517 | 10/1991 | Fenici . |
| 5,081,993 | 1/1992 | Kitney et al. . |
| 5,104,393 | 4/1992 | Isner et al. . |
| 5,154,501 | 10/1992 | Svenson et al. . |
| 5,156,151 | 10/1992 | Imran . |
| 5,158,092 | 10/1992 | Glace . |
| 5,161,536 | 11/1992 | Vilkomerson et al. . |
| 5,172,699 | 12/1992 | Svenson et al. . |
| 5,220,924 | 6/1993 | Frazin . |
| 5,222,501 | 6/1993 | Ideker et al. . |
| 5,246,016 | 9/1993 | Lieber et al. . |
| 5,246,438 | 9/1993 | Langberg ............................... 607/122 |
| 5,281,213 | 1/1994 | Milder et al. . |
| 5,295,484 | 3/1994 | Marcus et al. . |
| 5,297,549 | 3/1994 | Beatty et al. . |
| 5,311,873 | 5/1994 | Savard et al. . |
| 5,335,663 | 8/1994 | Oakley . |
| 5,341,807 | 8/1994 | Nardella . |
| 5,391,199 | 2/1995 | Ben-Haim . |
| 5,433,198 | 7/1995 | Desai . |
| 5,450,846 | 9/1995 | Goldreyer . |
| 5,487,385 | 1/1996 | Avitall . |
| 5,487,391 | 1/1996 | Panescu . |
| 5,529,067 | 6/1996 | Larsen et al. . |
| 5,582,609 | 12/1996 | Swanson . |
| 5,605,159 | 2/1997 | Smith et al. ............................ 600/515 |
| 5,741,249 | 4/1998 | Moss et al. ............................ 607/101 |
| 5,782,824 | 7/1998 | Abela et al. ............................ 607/122 |
| 5,792,140 | 8/1998 | Tu et al. . |

OTHER PUBLICATIONS

Hauer et al., Endocardial Catheter Mapping: Wire Skeleton Techniques for Representation of Computed Arrhythmogenic Sites Compared with Intraoperative Mapping, *Circulation*, vol. 74, No. 6, pp. 1346–1354, Dec. 1986.

Pogwizd et al., Reentrant and Nonreentrant mechanisms Contribute to Arrhythmogenesis During Early Myocardial Ischemia: Results using Three–Dimensional Mapping, *Circulation Research*, vol. 61, No. 3, pp. 352–371, Sep. 1987.

Huang et al., Radiofrequency Catheter Ablation of the Left and Right Ventricles: Anatomic and Electrophysiologic Observations, *Pace* vol. 11, pp. 449–459, Apr. 1988.

Jackman et al., New Catheter Technique for Recording Left Free–Wall Accessory Atrioventricular Pathway Activation, *Circulation* vol. 78, No. 3, pp. 598–611, Sep. 1988.

Pagé, Surgical Treatment of Ventricular Tachycardia: Regional Cryoablation Guided by Computerized Epicardial and Endocardial Mapping, *Circulation* vol. 80, (Supplement I), No. 3, pp. I–124–I–134, Sep. 1989.

Tweddel et al., Potential Mapping in Septal Tachycardia: Evaluation of a New Intraoperative Mapping Technique, *Circulation* vol. 80, (Supplement I), No. 3, pp. I–97–I–108, Sep. 1989.

Shenasa et al., Cardiac Mapping. Part I: Wolff–Parkinson–White Syndrome *Pace*, vol. 13, pp. 223–230, Feb. 1990.

Scheinman et al., Current Role of Catheter Ablative Procedures in Patients with Cardiac Arrhythmias, *Circulation* vol. 83, No. 6, pp. 2146–2153, Jun. 1991.

Buckles et al., Computer–Enhanced Mapping of Activation Sequences in the Surgical Treatment of Supraventricular Arrhythmias, *Pace* vol. 13, Pt. 1, pp. 1401–1407, Nov. 1990.

Tanigawa et al., Prolonged and Fractionated Right Atrial Electrograms During Sinus Rhythm in Patients with Paroxysmal Atrial Fibrillation and Sick Sinus Node Syndrome, *Journal of American College of Cardiologists* vol. 17, No. 2, pp. 403–408, Feb. 1991.

Kaltenbrunner et al., Epicardial and Endocardial Mapping of Ventricular Tachycardia in Patients with Myocardial Infarction, *Circulation* vol. 83, No. 3, pp. 1058–1071, Sep. 1991.

Massé et al., A Three–Dimensional Display for Cardiac Activation Mapping, *Pace*, vol. 14, Pt. 1, pp. 538–545, Apr. 1991.

Desai et al., Orthogonal Electrode Catheter Array for Mapping of Endocardial Focal Site of Ventricular Activation, *Pace* vol. 14, Pt. 1, pp. 557–574, Apr. 1991.

Pollak et al., Intraoperative Identification of a Radiofrequency Lesion Allowing Validation of Catheter Mapping of Ventricular Tachycardia with a Computerized Balloon Mapping System, *Pace* vol. 15, pp. 854–858, Jun. 1992.

Chen et al., Reappraisal of Electrical Cure of Atrioventricular Nodal Reentrant Tachycardia—Lesions from a Modified Catheter Ablation Technique *International Journal of Cardiology*, vol. 37, pp. 51–60, 1992.

Chen et al., Radiofrequency Catheter Ablation for Treatment of Wolff–Parkinson–White Syndrome—Short– and Long–term Follow–up *International Journal of Cardiology*, vol. 37, pp. 199–207, 1992.

Scheinman, North American Society of Pacing and Electrophysiology (NASPE) Survey of Radiofrequency Catheter Ablation: Implications for Clinicians, Third Party Insurers, and Government Regulatory Agencies, *Pace* vol. 15, pp. 2228–2231, Dec. 1992.

Silka et al., Phase Image Analysis of Anomalous Ventricular Activation in Pediatric Patients with Preexcitation Syndromes or Ventricular Tachycardia, *American Heart Journal* vol. 125, No. 2, Pt. 1, pp. 372–380, Feb. 1993.

Josephson, *Clinical Cardiac Electrophysiology: Techniques and Interpretations*, 2nd Ed. pp. 566–580, 608–615, 770–783, Lea & Febiger, Malvern Pa., 1993.

Kuchar et al., Electrocardiographic Localization of the Site of Ventricular Tachycardia in Patients with Prior Myocardial Infarction, *JACC*, vol. 13, No. 4, pp. 893–900, 1989.

Holt et al., Ventricular Arrhythmias—A Guide to Their Localization, *British Heart Journal*, vol. 53, pp. 417, 430, 1985.

Wolf, P.A., Dawber, T.R., Thomas, H.E. Jr., Kannel, W.B., Epidemiologic assessment of chronic atrial fibrillation and the risk of stroke: The Framingham Study, *Neurology*, 1978 (vol. 28), pp. 373–375.

Cox, J.L., Schuessler R.B., Boineau J.B., in *Surgery for Atrial Fibrillation, Cardiac Surgery; State of the Art Reviews*, 1990 (vol. 4), pp. 207–217.

Williams, J.M., Ungerleider, R.M., Lofmand, J.K., Cox, J.L., Left Atrial Isolation: A New Technique for the Treatment for Supraventricular Arrhythmias, *Journal of Thoracic Cardiovascular Surgery*, 1980 (vol. 80), pp. 373–380.

Guiraudon G.N., Campbell C.S., Jones D.L,. McLellan D.G., and MacDonald J.L., Combined Sino–atrial Node Ventricular Node Isolation: A Surgical Alternative to AV Node Ablation in Patients with Atrial Fibrillation (abstract), *Circulation*, 1985(72), pp. 111–220.

Haines, D.E., McRury, I.A., Whayne, J.G., and Fleischman, S.D., Atrial Radiofrequency Ablation: The Use of a Novel Deploying Loop Catheter Design to Create Long Linear Lesions (abstract), *Circulation*, 1994, (90,4), Part 2, pp. 1–335.

Seifert, M.J., Friedman, M.F., Selke, F.W., and Josephson, M.E., Radiofrequency Maze Ablation for Atrial Fibrillation (abstract), *Circulation*, 1994 (90,4), Part 2, pp. 1–595.

Cox et al., Surgical Interruption of Atrial Reentry as a Cure for Atrial Fibrillation, Olsson, S.B., Allessie, M.A., Campbell, R.W.F. (editors), Atrial Fibrillation: Mechanisms and Therapeutic Strategies, Futura Publishing Co., Inc., Armonk, NY, 1994.

Swartz, J.F, Pellersels, G., Silvers, J., Patten, L., and Cervantez, D., A Catheter Based Curative Approach to Atrial Fibrillation in Humans (abstract) Circulation, 1994 (90,4), Part 2, p. I–335.

Gregory W. Botteron and Joseph M. Smith, "A Technique for Measurement of the Extent of Spatial Organization of Atrial Activation During Atrial Fibrillation in the Intact Human Heart," in *IEEE Transactions on Biomedical Engineering* 12 (Jun. 1995), pp. 579–586.

Gregory W. Botteron and Joseph M. Smith, "Quantitative Assessment of the Spatial Organization of Atrial Fibrillation in the Intact Human Heart," in *Circulation* 93 (Feb. 1, 1996), pp. 513–518.

T. Bruce Fergusen, Jr., and James L. Cox, "Surgery for Atrial Fibrillation," in *Cardiac Electrophysiology: From Cell to Bedside*, Second Edition, Douglas P. Zipes and Jose Jalife, eds., (W.B. Saunders Company, 1995), pp. 1563–1576.

CARDIAC ABLATION CATHETER USING CORRELATION MEASURE

RELATED APPLICATIONS

This application is a Continuation-in-Part of U.S. patent application Ser. No. 08/476,200, filed Jun. 7, 1995, now U.S. Pat. No. 5,718,241, whose disclosure is incorporated herein by reference.

FIELD OF THE INVENTION

The present invention relates generally to cardiac therapeutic devices and methods, and specifically to catheter devices for treating electrical disorders of the heart by endocardial ablation.

BACKGROUND OF THE INVENTION

Atrial fibrillation (AF) is a well-known disorder of the heart, which causes hemodynamic efficiency to be reduced and, in serious cases, can lead to cardiac embolization, stroke, ventricular arrhythmias and other potentially fatal complications.

AF is frequently engendered by abnormal electrical conduction paths within the heart muscle. Normally, electrical activation signals are conducted in an orderly way through the atrium and into the ventricle, passing each point in the heart only once in each heart cycle. Electrical activation signals at different locations in the heart are well correlated, taking into account normal propagation delays from one region of the heart to another. In response to local activation signals, the atrial muscle fibers contract in proper synchrony, to pump blood through the atrium. In AF, however, this orderly contraction is lost, it is believed, as multiple, changing, spatially disorganized activation wavelets sweep across the surface of the atria, resulting in irregular patterns of electrical activation. A given atrial muscle fiber is activated to contract multiple times in each heart cycle, and fibrillation takes the place of normal contraction.

These phenomena are described in detail by Gregory W. Botteron and Joseph M. Smith in an article entitled, "A Technique for Measurement of the Extent of Spatial Organization of Atrial Activation During Atrial Fibrillation in the Intact Human Heart," in *IEEE Transactions on Biomedical Engineering* 12 (June 1995), pages 579–586, and in a second article entitled, "Quantitative Assessment of the Spatial Organization of Atrial Fibrillation in the Intact Human Heart," in *Circulation* 93 (Feb. 1, 1996), pages 513–518. Both of these articles are incorporated herein by reference.

Figure 1:
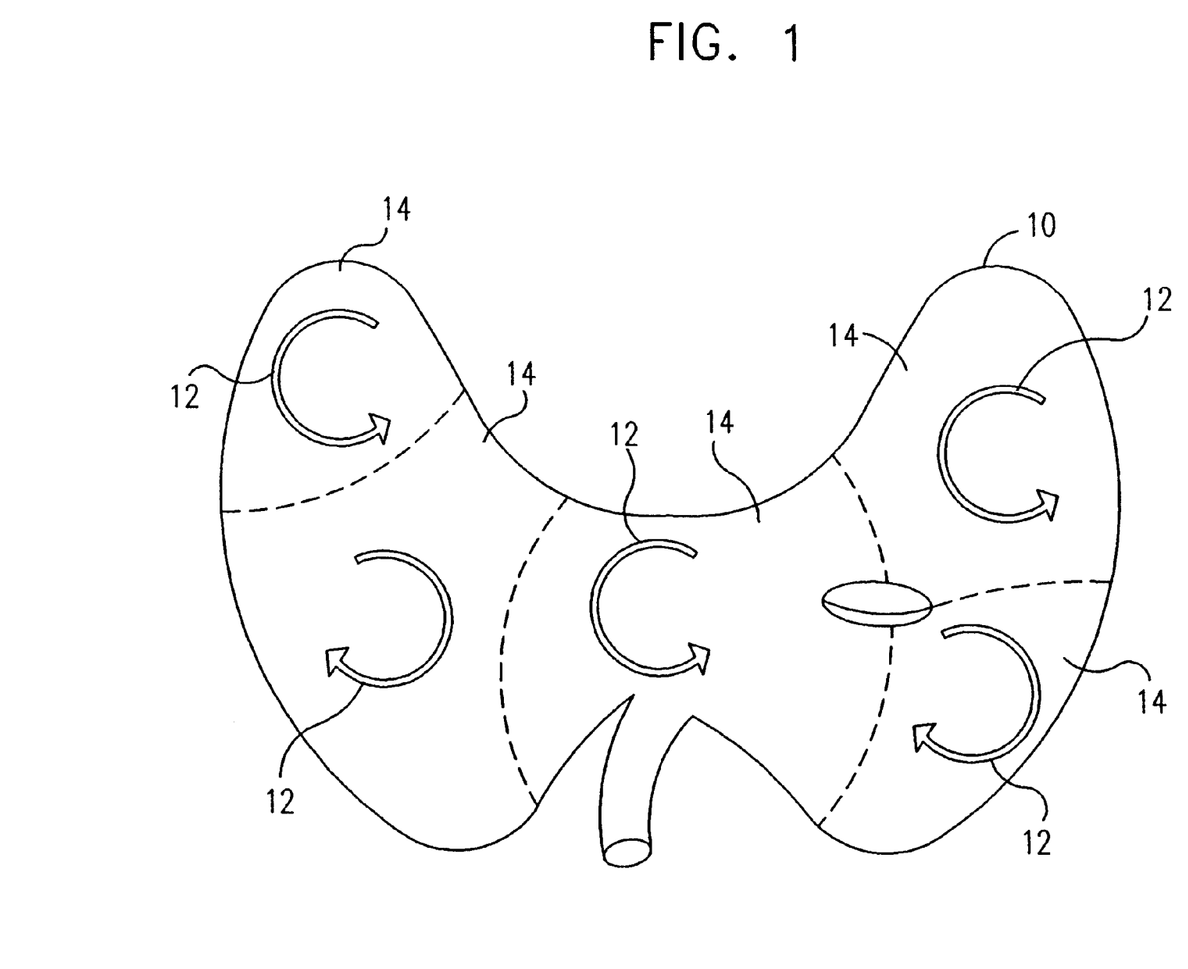
FIG. 1 is a schematic illustration of atrial tissue undergoing fibrillation, useful in understanding the principles of the present invention.

FIG. 1 schematically illustrates abnormal activation paths as encountered in atrial tissue 10 of a heart undergoing AF, following the description of Botteron and Smith. Multiple wavelets 12 are generated by reentrant activation signals, following circuitous paths in tissue 10. Each wavelet dominates a corresponding one of a plurality of spatial domains 14, so that within a given domain, the activation signals will generally be highly mutually correlated, while there will be little or no correlation between signals in different domains. It will be understood that the boundaries between domains 14, shown as dashed lines in the figure, are generally not fixed. Rather, the paths of wavelets 12 and domains 14 typically vary over time.

The minimum size of any one of the domains 14 is generally controlled by the minimum circumference of the circle described by the corresponding wavelet 12, which is roughly equal to a tissue dimension value D (referred to by Botteron and Smith as the tissue wavelength), given by the product of the tissue's conduction velocity and its refractory period. Typically D is on the order of 18 mm.

It will be appreciated that electrical activation signals at two locations in mutual proximity, within the same domain 14, will generally be well correlated. This correlation has been found to drop off inversely, generally exponentially, as a function of distance, so that in conditions of AF, signals at more distant locations, in different domains, are poorly correlated. By comparison, under conditions of orderly conduction within the heart tissue, the electrical activation signals will be well-correlated over substantially the entire heart, taking into account normal conduction delays between one location in the heart and another.

Although drug therapy or implantation of a pacemaker is frequently useful in controlling AF, when these methods are unsuccessful, the preferred method of treatment of the condition is to invasively interrupt the abnormal conduction paths in the heart. Preferably, a catheter having an RF ablation electrode is passed percutaneously through a blood vessel into the atrium of the heart. The electrode at the catheter tip is brought into contact with one or more sites in the endocardium where an abnormal conduction path is believed to pass, and the electrode is activated to ablate the site(s) and, it is hoped, break the abnormal path(s).

Generally, however, it is difficult or impossible to know the precise abnormal conduction path. Furthermore, even if an abnormal path is broken at one site, other abnormal paths may exist or new paths may arise at other sites, which paths will cause the AF to continue even after the one or more sites in the endocardium are ablated. In response to this difficulty, some cardiologists and cardiac surgeons have used a "maze procedure," as described, for example, by T. Bruce Ferguson, Jr., and James L. Cox in an article entitled, "Surgery for Atrial Fibrillation," in *Cardiac Electrophysiology: From Cell to Bedside*, Second Edition, Douglas P. Zipes and Jose Jalife, eds., (W. B. Saunders Company, 1995), pages 1563–1576, which is incorporated herein by reference. In this procedure, multiple elongated strips in the endocardium are surgically cut or ablated in a direction generally parallel to the desired, normal, direction of conduction in the atrium. This procedure is time-consuming and causes far more damage to the endocardium than would be necessary if the abnormal paths could be selectively ablated.

U.S. Pat. No. 5,450,846, whose disclosure is incorporated herein by reference, describes a catheter, which may be repeatedly repositioned inside the heart, comprising an ablator at its distal tip and pairs of non-contacting sensing electrodes arrayed around the outside of the catheter near the distal end. Each electrode pair senses local electrogram signals generated in the endocardium in a small area near the side of the catheter that it faces. Differences in the activation times in the signals sensed by the pairs of electrodes are used to estimate the direction of the activation vector in the vicinity of the catheter, so as to guide the operator in positioning the ablator. This catheter is useful, however, only when electrical activation paths within the heart are relatively orderly, and not in the chaotic jumble of activation paths that generally characterizes AF.

SUMMARY OF THE INVENTION

It is an object of some aspects of the present invention to provide devices and methods for diagnosis and mapping of abnormal conduction paths in the heart of a subject.

It is another object of some aspects of the present invention to provide devices and methods for selective ablation of sites in the heart tissue of a subject so as to interrupt such abnormal conduction paths.

It is a further object of some aspects of the present invention to provide devices and methods for ablating a site in the heart tissue in the vicinity of an abnormal conduction path and measuring electrical signals in the heart adjacent to the site so as to determine whether the path has been interrupted.

In one aspect of the present invention, the effectiveness of the ablation in interrupting the abnormal path is determined by observing and comparing a correlation between the electrical signals at two points on either side of the site, before the ablation and again after the ablation. If the correlation is substantially changed, then the ablation is judged to have been effective.

In preferred embodiments of the present invention, a cardiac catheter has a distal end that is inserted into a chamber of the heart of a subject. The catheter includes an ablation device, preferably an RF ablation electrode, near its distal end, and first and second electrodes, preferably bipolar electrodes, for sensing electrical signals in the heart tissue. Preferably, one electrode is positioned on either side of the ablation device, spaced by a suitable distance. The proximal end of the catheter, outside the subject's body, is connected to a control console, which receives signals from the electrodes and includes signal processing circuitry for analyzing the signals, and which also supplies energy to the ablation device upon command of a user.

Preferably, the first and second electrodes are spaced far enough apart on the catheter, and the distal end of the catheter is suitably positioned in contact with the endocardium, so that there will be a measurable propagation delay between the activation signals at the locations of the first and second electrodes under conditions of normal conduction. This normal propagation delay is different from the delay encountered in the presence of AF. On the other hand, since under conditions of AF, the correlation of the signals generally decreases exponentially with the distance between the electrodes, the electrodes should be close enough together to sense this correlation. Thus, the distance between the first and second electrodes is preferably larger than the width of lesions to be created in the heart tissue by the ablation device, but smaller than the tissue dimension value D, as described in the Background of the Invention.

In some preferred embodiments of the present invention, the catheter further includes a position sensor, which is used to determine the position of the distal end of the catheter and/or the ablation device relative to the heart or to another external frame of reference. Preferably, the position sensor comprises one or more coils, which generate electrical signals in response to an externally-applied magnetic field, for example, as described in PCT patent publication number WO96/05768 and in U.S. Pat. No. 5,391,199, whose disclosures are incorporated herein by reference. Alternatively, other types of position sensors known in the art may be used.

In preferred embodiments of the present invention, the catheter is manipulated so as to position the ablation device in contact with the endocardium at the site of a suspected abnormal conduction path. First and second pre-ablation signals, responsive to the heart's activation signals, are received from the first and second electrodes, respectively, preferably simultaneously, or alternatively successively, and a correlation coefficient of the first and second pre-ablation signals is computed. The ablation device is then activated so as to ablate the endocardium at the site, preferably by applying RF energy thereto.

After the ablation is completed, and the ablation device is de-activated, first and second post-ablation signals are respectively received from the first and second electrodes, and the correlation coefficient is again computed. If the pre- and post-ablation correlation coefficients are substantially the same, the ablation is determined to have been insufficient to interrupt the abnormal conduction path, either because the tissue adjacent to the ablation device was not fully ablated, or because, although the site was ablated, reentrant wavelets continue to propagate around the site. The above process must then be repeated at the same site or at another site in the endocardium. If the post-ablation correlation coefficient is substantially less than or greater than the pre-ablation coefficient, however, the ablation is considered to have been effective in interrupting the abnormal path.

Preferably, the correlation coefficient of the first and second pre-ablation signals (and concomitantly the first and second post-ablation signals) is determined by performing time-domain correlation calculations, for example, by multiplying the first and second signals together and integrating the product over one or more cardiac cycles. Further preferably, a variable time delay between the first and second signals is introduced in determining the pre-ablation correlation coefficient, and the time delay value that maximizes the correlation coefficient is found. This same time delay value is preferably used in determining the post-ablation correlation coefficient. A similar technique, which may also be used in the present invention, is described in the above-mentioned article in *Circulation*. If the first and second signals are acquired successively, the acquisition of the signals is preferably synchronized with the heart beat, and the second signal is time-shifted relative to the first signal using the heart beats as a registration points, before performing the correlation calculation.

Alternatively or additionally, the correlation coefficients may be used to determine a time shift of the second pre-ablation signal relative to the first pre-ablation signal, and similarly of the second post-ablation signal relative to the first. If the post-ablation time shift is found to differ substantially from the pre-ablation time shift, the ablation is considered to have been effective in interrupting the abnormal path. These time shifts may be determined, for example, by using the first signal as a fixed template, variably phase-shifting the second signal relative to the template, and repeatedly calculating the correlation coefficient until the time shift that gives the maximum coefficient is found. Preferably, the signals are first filtered before performing the calculations, most preferably band-pass filtered, so as to separate the high-frequency activation waveforms from other components of the signals that could reduce the accuracy of correlation coefficients that are determined.

Further alternatively, the first and second pre- and post-ablation signals may be transformed to the frequency domain, for example using the well-known Fast Fourier Transforms (FFT). Frequency correlation coefficients may then be calculated between the signals and used to determine the effectiveness of the ablation, described above.

In some preferred embodiments of the present invention, the catheter includes a pre-ablation testing device, adjacent to the ablation device, near its distal end, as described, for example, in U.S. Pat. No. 5,281,213, which is incorporated herein by reference. Preferably, the testing device comprises a miniature cooler, for example a thermoelectric cooler, which is operated from the control console to cool the suspected site of the abnormal conduction path. As described in the '213 patent, cooling the heart tissue to a temperature of approximately 5° C. reversibly interrupts the conduction of activation signals therethrough. Correlation coefficients before and after cooling, or other reversible testing, are calculated and used as described above, to assess the potential effectiveness of ablating the site, before the ablation device is activated. In this way damage to the heart tissue may be limited to that which is actually needed and effective to interrupt abnormal conduction paths.

Although preferred embodiments are described herein with reference to treatment of AF, the principles and methods of the present invention may also be applied to treat other heart disorders, for example, atrial flutter. Those skilled in the art will also appreciate that other methods of treating abnormal heart tissue may also be used, particularly other methods of tissue ablation, in place of RF ablation as described herein.

Furthermore, although the preferred embodiments described herein provide for both diagnosis and ablation of abnormal conduction paths, it will be appreciated that the principles of the present invention may be applied to perform diagnosis and/or mapping of electrical conduction in the heart, without necessarily treating the abnormal conduction paths.

There is therefore provided, in accordance with a preferred embodiment of the present invention, a method for determining the effectiveness of treatment of abnormal conduction paths in the heart of a subject, including:
  inserting a probe into the heart;
  positioning the probe at a site in the endocardium;
  sensing respective first and second electrical activation signals, using the probe, at first and second points in the endocardium in a vicinity of the site;
  determining a correlation measure of the first and second activation signals sensed by the probe, indicative of the presence of an abnormal conduction path in the vicinity of the site; and
  interrupting conduction at the site using the probe.

Preferably, sensing the electrical activation signals includes sensing respective first and second signals before interrupting the conduction and sensing respective first and second signals after interrupting signals before interrupting conduction is compared with that of the first and second signals after interrupting conduction.

The correlation measures are preferably compared by finding a first correlation measure using the first and second signals before interrupting conduction; finding a second correlation measure using the first and second signals after interrupting conduction; and comparing the first and second correlation factors, preferably by calculating a difference of the first and second correlation measures, to determine effectiveness of the treatment.

Preferably, determining the correlation measure includes performing a time-domain correlation computation and, more preferably, computing a phase shift to give a desired correlation value.

Alternatively or additionally, determining the correlation measure includes computing frequency spectra of the first and second signals.

Preferably, interrupting conduction includes transferring energy between the probe and the site, more preferably ablating the site. Ablating the site preferably includes ablating a generally linear area in the vicinity of the site or, alternatively, ablating an area having a complex shape in the vicinity of the site.

Further alternatively, transferring energy between the probe and the site includes cooling the site. The effect of cooling the site on the correlation of the signals is preferably determined, and the site is ablated responsive to the effect.

There is further provided, in accordance with a preferred embodiment of the present invention, a method for mapping electrical activity in the heart of a subject, including:
  inserting a probe into the heart;
  positioning the probe in sequence at a plurality of sites in the endocardium;
  sensing respective first and second electrical activation signals, using the probe, at first and second points in the vicinities of each of the plurality of sites;
  processing the signals sensed by the probe to determine a correlation measure of the respective first and second activation signals at each of the plurality of sites; and
  producing a map of the correlation measures, indicative of the locations of abnormal conduction paths.

Preferably, the method further includes:
  positioning the probe in a vicinity of a lesion ablated in the tissue at one of the sites, after producing the map;
  receiving electrogram signals, using the probe, from at least two points in the vicinity of the lesion after ablation thereof;
  processing the signals received by the probe to determine the correlation measure between the signals at the points in the vicinity of the lesion after the ablation; and
  comparing the measure determined after the ablation to the measure determined before the ablation to determine the effectiveness of the treatment.

There is also provided, in accordance with another preferred embodiment of the present invention, a method for determining the effect of ablation on excitable tissue, including:
  positioning a probe in a vicinity of a lesion ablated in the tissue;
  receiving electrogram signals, using the probe, from at least two points in the vicinity; and
  processing the signals received by the probe to determine a correlation measure between the signals at the points.

Preferably, the correlation measure is compared with a previous correlation measure determined by processing signals received from at least two of the at least two points before ablating the tissue.

In a preferred embodiment of the present invention, receiving signals from the at least two points includes receiving signals from a plurality of pairs of points, and processing the signals includes producing a correlation map of the tissue, indicative of the effect of the ablation.

Preferably, receiving electrogram signals includes receiving bipolar electrogram signals.

Further preferably, processing the signals to determine the correlation measure includes performing a time-domain correlation computation and, preferably, computing a phase shift to give a correlation value.

Additionally or alternatively, processing the signals includes computing frequency spectra of the signals.

There is also provided, in accordance with a preferred embodiment of the present invention, apparatus for endocardiac therapy, including:
  an elongate probe for insertion into the heart of a subject, the probe having distal and proximal ends and including an ablation device for ablating heart tissue and at least two sensing electrodes, preferably bipolar electrodes, for sensing activation signals in the heart tissue adjacent to the ablation device; and
  signal analyzer circuitry, which receives the activation signals from the probe and calculates a correlation measure thereof.

Preferably, the probe includes a position sensor adjacent to the ablation device, which generates signals responsive to the position of the probe with respect to an external frame of reference.

Further preferably, the ablation device includes an ablation electrode, and one of the at least two sensing electrodes includes the ablation electrode.

Preferably, the ablation device is positioned over the outer surface of the probe, substantially covering the distal end thereof.

Additionally or alternatively, the ablation device and electrodes are positioned along an outer, radial surface of the probe, wherein one electrode is axially proximal to the ablation device, and the other electrode is axially distal to the ablation device.

Preferably, the system includes a cooler, for cooling the heart tissue, adjacent to the ablation device.

Alternatively, the cooler is thermally coupled to the ablation device, which cools the heart tissue.

There is further provided, in accordance with a preferred embodiment of the present invention, apparatus for determining the effectiveness of treatment of abnormal conduction in the heart of a subject, including:

an elongate probe for insertion into the heart of the heart, the probe having distal and proximal ends and including at least two sensing electrodes, preferably bipolar electrodes, near the distal end of the probe, for sensing activation signals in the heart tissue; and signal analyzer circuitry, which receives and determines a correlation measure of the activation signals and compares a first correlation measure determined before the treatment with a second correlation measure determined after the treatment.

Preferably, the probe includes a position sensor near the distal end thereof, which generates signals responsive to the position of the probe with respect to an external frame of reference.

Preferably, the probe is positioned at a plurality of locations in the heart, and the signal analyzer circuitry produces a map of the correlation measures determined at the plurality of locations.

The present invention will be more fully understood from the following detailed description of the preferred embodiments thereof, taken together with the drawings in which:

DETAILED DESCRIPTION OF PREFERRED EMBODIMENTS

Figure 2A:
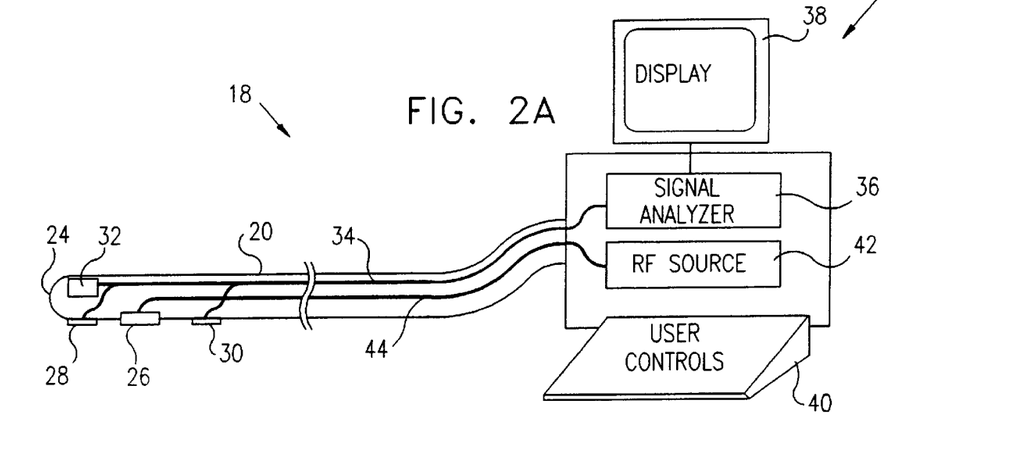
FIG. 2A is a schematic illustration of a catheter system, in accordance with a preferred embodiment of the present invention.

Reference is now made to FIG. 2A, which schematically illustrates a catheter system 18, including a catheter 20, for insertion into the heart of a subject, and an accompanying control unit 22 coupled to the proximal end of the catheter, in accordance with a preferred embodiment of the present invention. Near its distal end 24, catheter 20 includes an ablation device 26, preferably an RF ablation electrode, and two electrodes 28 and 30, preferably bipolar electrodes, for sensing electrical activation signals in the endocardium. Preferably one electrode 28 is distal to ablation device 26, and the other electrode 30 is proximal to it.

Catheter 20 preferably also includes a position sensor 32, similarly adjacent to its distal end 24. Sensor 32 preferably comprises a plurality of coils, which generate signals responsive to externally-applied magnetic fields, as described in the above-mentioned WO96/05768 PCT patent publication. The magnetic fields are preferably generated by field generators outside the body of the subject (not shown in the figures). The signals generated by the coils are used to continuously determine six-dimensional position and orientation information regarding distal end 24 of catheter 20. Other types of position sensors known in the art, which are capable of determining three-dimensional position coordinates and one or two angular orientation coordinates, can also be used in the practice of the invention.

Activation signals sensed by electrodes 28 and 30 and position signals generated by position sensor 32 are conveyed via signal wires 34 to signal analyzer circuitry 36 in console 22. Circuitry 36 processes the signals from electrodes 28 and 30 and calculates correlation coefficients, as will be described below. Circuitry 36 also determines the position of distal end 24 of catheter 20.

Console 22 preferably also includes a display 38, on which the activation signal and position information is presented to a user, and user controls 40. The user controls are used to activate and de-activate an RF source 42 as desired, which source provides RF power to ablation electrode 26 over power wires 44. Preferably, catheter 20 and console 22 also include means, known in the art, for steering distal end 24 of catheter 20, preferably controlled via the console.

Figure 2B:
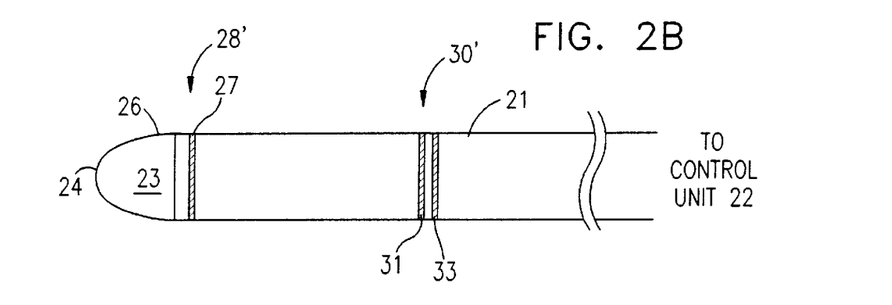
FIG. 2B is a schematic illustration of the distal portion of a catheter, in accordance with an alternative preferred embodiment of the present invention.

FIG. 2B schematically illustrates the distal portion of a catheter 21, which may be used in system 18 in place of catheter 20, in accordance with an alternative preferred embodiment of the present invention. For clarity of illustration, only external elements of catheter 21 are shown in FIG. 2B. It will be understood, however, that catheter 21 includes wires 34 and 44 and, preferably, contains a position sensor, such as sensor 32, and a steering device, substantially as described above. Catheter 21 is preferably 1–3 mm in diameter. Ablation electrode 26 comprises a conductive external layer 23 on catheter 21, extending proximally along the catheter from distal end 24 for a length of 2–8 mm. A ring electrode 27, having a width of 1–2 mm, surrounds catheter 21 proximal to device 26, with a non-conducting gap of preferably about 1–2 mm between device 26 and electrode 27. Two more ring electrodes 31 and 33, similar to electrode 27, surround catheter 21, preferably at a distance of about 8–18 mm, most preferably about 12 mm, from electrode 27 and with a gap of about 1–2 mm between electrodes 31 and 33.

In the preferred embodiment shown in FIG. 2B, a bipolar electrode 28' comprises ablation electrode 26 and ring electrode 27, mutually coupled in bipolar fashion, as is known in the art. A second bipolar electrode 30' similarly comprises ring electrodes 31 and 33. During the phase of operation of system 18 in which circuitry 36 receives and processes activation signals from electrodes 28' and 30', device 26 is coupled via signal wires 34 to the circuitry, and thus functions as a sensing electrode. During ablation, device 26 is coupled to RF source 42 and, preferably, disconnected from circuitry 36, so that the device functions as an ablation electrode. In the description of the present invention that follows, references to electrodes 28 and 30 will be understood to apply as well, wherever appropriate, to electrodes 28' and 30', mutatis mutandis.

Under normal conditions of sinus rhythm, the electrical activation signals measured at two locations in the endocardium, for example using electrodes 28 and 30, will generally exhibit a high degree of correlation. This correlation is reflected in the two signals having similar frequency spectra and in the normalized correlation coefficient $\overline{C}$ of the two signals having a value close to one, where $$\overline{C} = \frac{\int_0^T E_1(t) E_2(t - \Delta) dt}{|E_1||E_2|} \quad (1)$$

in which $E_1(t)$ and $E_2(t)$ are the respective activation signals sensed by electrodes 28 and 30; T is an integration time preferably corresponding to a number of cardiac cycles; $\Delta$ is a delay much smaller than T, corresponding generally to the difference in the arrival time of the activation signal at the position of electrode 28 from that at electrode 30; and $$|E_i| = \left[ \int_0^T E_i^2(t) dt \right]^{\frac{1}{2}}. \quad (2)$$

In the preferred embodiments of the present invention described above with reference to FIGS. 2A and 2B, under typical conditions, in the absence of fibrillation, the delay $\Delta$ will be approximately in the range 3–240 msec, given by the quotient of the distance separating electrodes 28 and 30, preferably about 12 mm, divided by the local conduction velocity in the heart, typically 0.05 to 4 m/sec. Preferably, circuitry 36 determines and resolves values of $\Delta$ down to a resolution limit less than or equal to 2 msec. For this purpose, the circuitry preferably includes a band-pass filter, which removes low-frequency background and high-frequency transients in the electrogram signals received by the electrodes, prior to performing correlation calculations, as well as other pre-correlation signal conditioning circuitry. For example, prior to the correlation calculation, the electrogram signals may be passed through a 40–250 Hz band-pass filter, followed by an absolute value operation and a 20 Hz low-pass filter, as described in the above-mentioned articles by Botteron and Smith.

As described above, the high correlation coefficient of the electrical activation signals is characteristic of the normal, cooperative contraction of the heart muscle fibers. In the presence of abnormal, parasitic conduction paths in the heart, however, as is the case in atrial fibrillation, this cooperative contraction is reduced or lost entirely within at least a portion of the heart muscle. Under these conditions, a high correlation coefficient between the activation signals sensed at two points in the endocardium may be indicative of the presence of an abnormal conduction path.

Thus, when AF is encountered or suspected, catheter 20 or 21 is, preferably, first used to create a correlation map of at least a portion of the atrium in which ablation is to take place. At each of a plurality of known positions in the atrium, circuitry 36 receives signals from electrodes 28 and 30 and determines the correlation between the signals. Preferably, the correlation mapping is performed in conjunction with measurements of the tissue conduction velocity and refractory period, so as to determine and map local values of the tissue dimension value, D, as described in the parent application to this one, U.S. Pat. No. 5,718,241, incorporated herein by reference.

In such a map, areas of normal conduction will generally be characterized by consistent, high correlation coefficients at an appropriate delay $\Delta$. At sites of parasitic conduction, however, the correlation coefficients will typically vary chaotically, and/or the delay $\Delta$ that gives a high correlation between the signals will differ from that expected for normal conduction. On the other hand, a consistently low correlation coefficient at a site may be indicative of a conduction block in the area of the site. After making the map, the sites of parasitic conduction are preferentially ablated, while areas of normal conduction or of conduction block are generally not ablated.

Figure 3:
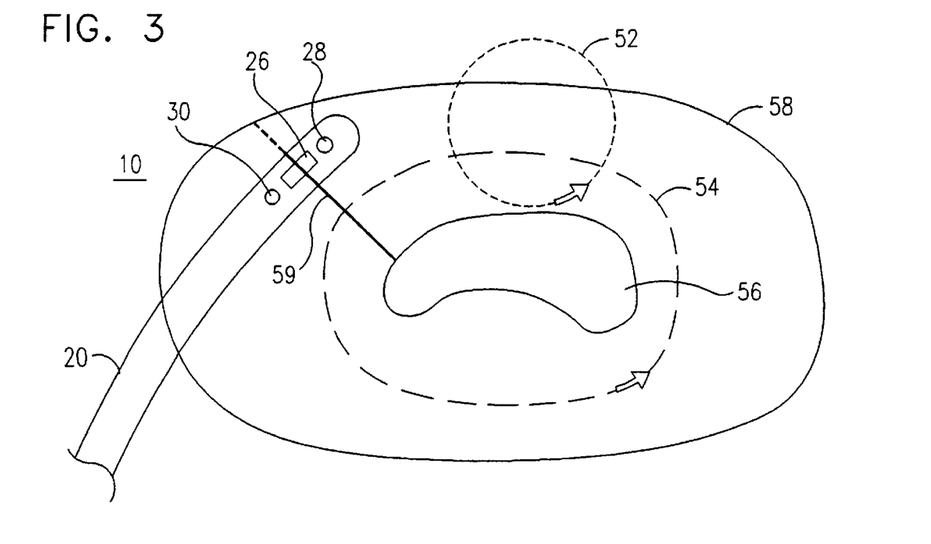
FIG. 3 is a schematic illustration showing the distal end of the catheter of FIG. 2A in contact with areas of abnormal electrical conduction in the heart tissue.

FIG. 3 schematically illustrates possible reentrant conduction paths 52 and 54 in the vicinity of a conduction block 56 in heart tissue 10, for example within the atrium of the heart as illustrated in FIG. 1, and the operation of catheter 20 in ablating portions of the heart tissue in relation to these paths. It will be understood that paths 52 and 54 represent only two out of many possible paths for wavelets 12 (as shown in FIG. 1). Such paths generally need only to have a length greater than the local dimension value D and a curvature no less than a minimum radius a, as described in the parent application. Paths 52 and 54 are generally not fixed conduction paths, but rather transient paths, along which activation signals may be conducted, either around block 56 (path 54) or adjacent to it (path 52). As described above, activation signals traveling along path 52 or 54 will cause muscle fibers in the path to be activated at inappropriate times, frequently with multiple activations during the period of a single heart beat, leading to fibrillation.

At the point in time illustrated in FIG. 3, catheter 20 is shown to have already ablated a circumferential ablation line 58 (referred to as a $\Psi$-type ablation line in the parent application), which interrupts path 52 and other, similar paths adjacent to block 56. Line 58 does not interrupt paths around block 56, such as path 54, however. Therefore, in FIG. 3, catheter 20 is shown in the course of ablating a radial ($\lambda$-type) ablation line 59. The catheter is positioned so that ablation electrode 26 can ablate a series of points in succession along line 59, until all paths such as path 54 have been interrupted. Preferably, position sensor 32 (shown in FIG. 2A, but omitted in FIG. 3 for simplicity) is used to position the catheter in the desired locations and to track the catheter's position as it is steered to various locations in the heart.

Before RF source 42 is activated, the correlation coefficient $\overline{C}$ between the signals sensed by electrodes 28 and 30 along path 54 generally has a relatively high value. As described above, this value will commonly fluctuate, due to variations in the reentrant conduction currents during AF. Preferably, the value of $\Delta$ in equation (1) is adjusted so as to maximize the value of $\overline{C}$.

When the RF source is activated, ablation electrode 26 selectively ablates the heart tissue adjacent to the electrode, thereby gradually extending line 59. After the ablation, signals are again sensed by electrodes 28 and 30, and the correlation coefficient $\overline{C}$ is calculated, preferably while maintaining $\Delta$ at its pre-ablation value, and compared to the pre-ablation coefficient. If the coefficient has not changed substantially, catheter 20 is repositioned, and line 59 is extended further. Once line 59 has been extended sufficiently, the correlation coefficient between the signals from electrodes 28 and 30 is generally substantially reduced. The reduction in the correlation coefficient indicates that path 54 has been successfully interrupted. On the other hand, if as a result of the ablation, normal conduction has come to prevail in place of AF in heart tissue 10 (at least in the portion of the tissue against which catheter 20 is positioned), the correlation coefficient will increase to a value close to 1 for an appropriate choice of $\Delta$.

Alternatively, it may occur that even after line 59 has been completely ablated, from block 56 to line 58, there is still a substantial correlation, indicative of reentrant paths, between the signals at electrodes 28 and 30. In this case, catheter 20 will preferably be repositioned to form an additional radial line, on the opposite side of block 56, for example, and the signal correlation measurements and ablation will be repeated. In either case, the use of catheter system 18 allows the progress of the ablation procedure to be tracked, assessed and adjusted in real time, so as to provide optimal treatment for AF while minimizing unnecessary damage to the heart tissue.

It will be understood that the types of conduction abnormalities and the geometries of ablation lines 58 and 59 in FIG. 3 are shown only by way of example. The principles of the present invention may be used to treat a wide range of abnormal conduction paths that arise in AF, include complex and irregularly-shaped paths. Thus, for example, catheter 20 may be used to ablate a group of sites defining a complex shape, in order to completely cut an abnormal path.

Ablation device 26 may comprise a standard ablation electrode, which generally produces ablation lesions at least 1 cm wide. In this case, electrodes 28 and 30 are placed about 2 cm apart. The average correlation coefficient between the signals sensed by these electrodes in the presence of AF, before ablation, will typically be no more than 0.3, since the correlation drops exponentially with distance, as described above (whereas in a normally-conducting heart, high correlation coefficients, approaching 1, are obtained even for mutually distant points, by appropriate choice of $\Delta$). Consequently, it may be difficult to observe the change in correlation that occurs after the ablation.

To overcome this difficulty, ablation device 26 is preferably configured to ablate thin lesions, preferably no more than 3 to 5 mm wide, such as those shown in FIG. 3. For this purpose, device 26 may comprise, for example, a thin ablation electrode or, alternatively, an optical device for applying laser irradiation to heart tissue 50, as is known in the art. Electrodes 28 and 30 are then preferably placed no more than about 1 cm apart. The average correlation coefficient between the signals sensed by the electrodes at this distance, under conditions of AF, will typically be about 0.8. Thus, changes in the correlation may be more easily and accurately observed.

Although FIG. 3 is drawn and described with reference to catheter 20, it will be understood that catheter 21, as shown in FIG. 2B, may be used in a substantially similar fashion. When catheter 21 is used, however, the area adjacent to bipolar electrode 28' is ablated by ablation device 26. Therefore, to measure the signal correlation post-ablation, catheter 21 should be advanced distally so that electrodes 28' and 30' are on opposite sides of the lesion that has been ablated. Alternatively, the catheter may be drawn back in a proximal direction, for example, to determine whether the ablation has enhanced conduction along a normal path on the proximal side of the lesion. In other cases, it may be sufficient to measure the signal correlation pre-ablation, to ascertain that abnormal conduction exists at the site to be ablated, and to forego the post-ablation measurement.

While in the preferred embodiment described above, the magnitude of the correlation coefficient $\overline{C}$, at a fixed value of $\Delta$, is used as the indicator of changes in the correlation between signals $E_1$ and $E_2$, in other preferred embodiments of the present invention, other indicators may be used. For example, a change in the relative phases of $E_1$ and $E_2$ may be determined, by finding a first delay value $\Delta_b$, which gives the highest value of $\overline{C}$ before ablation, and then finding a second delay value $\Delta_a$, which gives the highest value of $\overline{C}$ after ablation, and comparing the two delay values.

Alternatively, frequency spectra of $E_1$ and $E_2$, $\epsilon_1(\omega)$ and $\epsilon_2(\omega)$ respectively, may be calculated before and after ablation, for example, by means of a Fast Fourier Transform (FFT). The correlation coefficient of $\epsilon_1$ and $\epsilon_2$ is then determined using a formula similar to equation (1), but with integration over $\omega$, rather than t, before and after ablation. Changes in the correlation coefficient are noted and used as described above. Other statistical properties of the spectra, as are known in the art, may similarly be analyzed and compared, before and after ablation, in order to assess the effectiveness of the ablation.

Preferably, signals $E_1$ and $E_2$ are simultaneously acquired by circuitry 36 from bipolar electrodes 28 and 30. Alternatively, if the signals are to be analyzed in the frequency domain, as described above, the two signals may be acquired in sequence, preferably in sequential heart cycles, both before and after ablation. This technique may afford greater ease in signal acquisition and reduction of the electrical component count. In this case, acquisition of the signals is preferably synchronized with the heart beat, for example using the QRS complex of the heart's ECG as a trigger pulse. This synchronization is generally necessary if the correlation of $E_1$ and $E_2$ is to be analyzed in the time domain, as described above in reference to equation (1). Synchronization may usually be dispensed with, however, if the correlation or other statistical analysis is performed in the frequency domain, as long as the FFT or other transform is taken over a period that is much longer than a single heart beat.

The present invention typically allows a physician to interrupt abnormal conduction paths more rapidly and with less unnecessary injury to the heart tissue than invasive methods known in the art, because it provides direct feedback as to the effectiveness of the operation at each site in the endocardium chosen for ablation. In the preferred embodiments of the present invention described above, however, there may still be sites in the heart tissue that are unnecessarily ablated.

Figure 4:
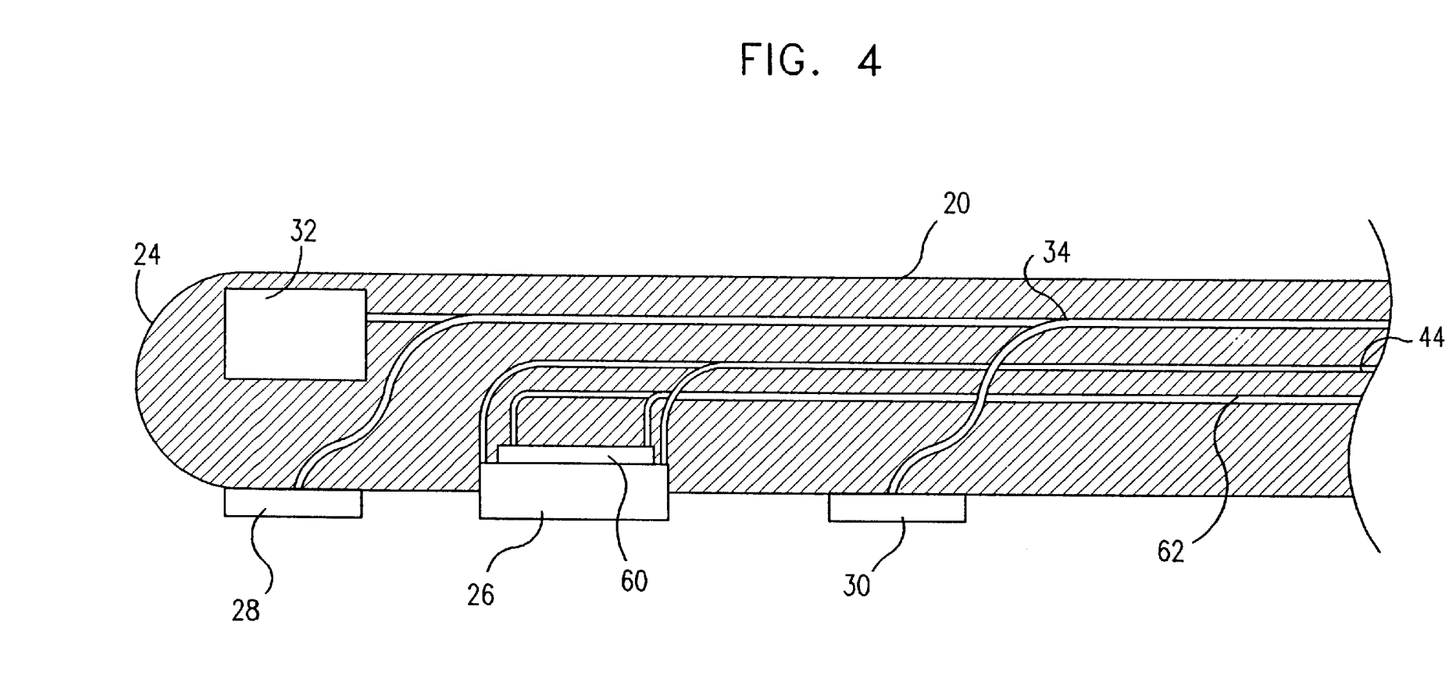
FIG. 4 is a schematic, sectional illustration of the distal end of a catheter, in accordance with another preferred embodiment of the present invention.

FIG. 4, therefore, schematically illustrates, in sectional view, another preferred embodiment of the present invention in which the potential effectiveness of ablating a suspected site of an abnormal conduction path in the heart tissue is reversibly evaluated before ablation. As shown in FIG. 4, catheter 20 is substantially similar to that shown in FIG. 1 and described with reference thereto, but with the addition of a thermoelectric cooler 60, which is thermally coupled to ablation electrode 26. Cooler 60 receives electrical power via wires 62 from a suitable power supply (not shown in the figures), as is known in the art, in console 22.

As in the preferred embodiments described earlier, catheter 20 as shown in FIG. 4 is positioned so that ablation electrode 26 is in contact with the endocardium at the site of a suspected abnormal conduction path. The correlation of activation signals sensed by bipolar electrodes 28 and 30 is measured by signal analyzer circuitry 36. Cooler 60 is then activated, by providing electrical current through wires 62, so as to cool ablation electrode 26, preferably to about $-10°$ C. The cooled electrode chills the heart tissue adjacent thereto to a suitable temperature, preferably around $5°$ C. As described, for example, in the above-mentioned U.S. Pat. No. 5,281,213, cooling the heart tissue to a temperature in this range prevents the tissue from responding to or conducting activation signals, as though the tissue had been ablated. Unlike ablation, however, when cooler 60 is de-activated or ablation electrode 26 is removed from contact with the tissue, and the tissue returns to a normal temperature of approximately 37° C., normal function and conduction by the tissue are restored.

Thus, when cooler 60 has been activated, and the tissue at the site of the suspected abnormality, adjacent to electrode 26, has been cooled to the desired temperature, the correlation of the activation signals sensed by bipolar electrodes 28 and 30 is again measured. If the correlation is determined to have changed substantially on account of the cooling, RF source 42 is then activated to permanently ablate the site and interrupt the abnormal path. On the other hand, if there is no substantial change in the correlation, the site is allowed to re-warm and return to normal function with no unnecessary injury to the tissue.

Although FIG. 4 shows thermoelectric cooler 60 located generally in contact with ablation electrode 26 and cooling the heart tissue through the electrode, it will be appreciated that other types of coolers, known in the art, may also be used. Moreover, the cooler may be placed in any convenient position alongside electrode 26, as long as it can adequately cool the tissue adjacent to the electrode. Other methods of reversibly interrupting the electrical conduction of the tissue may similarly be used, for example, by locally injecting a conduction-inhibiting drug into the endocardium.

It will also be understood that although the above preferred embodiments include an RF electrode for ablation, other ablation devices and methods known in the art, for example, microwave ablation or alcohol injection, may equally be used.

In the preferred embodiments of the present invention shown in the figures and described above, ablation electrode 26 is disposed axially along a radial outer surface of catheter 20, with bipolar electrodes 28 and 30 similarly disposed, one distal and one proximal. In other preferred embodiments of the present invention, however, electrodes 26, 28 and 30 may be placed in any convenient configuration.

For example, electrodes 26, 28 and 30 may be suitably mounted on a substantially rigid structure at the distal end of catheter 20, as described, for example, in PCT patent application no. PCT/IL97/00009, filed Jan. 8, 1997, which is assigned to the assignee of the present patent application and whose disclosure is incorporated herein by reference. Furthermore, three or more bipolar sensing electrodes may be mounted on the structure, and the mutual correlations of the activation signals that they receive may be compared in order to more precisely position the ablation electrode. The correlation information may be combined with conduction velocity information, determined as described in the '009 PCT application. The combined information is preferably used for mapping electrical activity in the heart before ablation treatment and, additionally or alternatively, for identifying suitable sites for ablation and determining the efficacy of ablation treatment carried out at the sites, as described herein.

It will be further appreciated that the preferred embodiments described above are cited by way of example, and the full scope of the invention is limited only by the claims.

I claim:

1. A method for assessing the effectiveness of treatment of abnormal conduction paths in the heart of a subject, comprising:

positioning a probe at a treatment site in the heart;

sensing respective first and second electrical signals, using the probe, at first and second points in the endocardium in a vicinity of the site; and determining a correlation measure of the first and second signals sensed by the probe, so as to detect an abnormal conduction path in the vicinity of the site.

2. A method according to claim 1, wherein determining the correlation measure comprises performing a time-domain correlation computation.

3. A method according to claim 1, wherein determining the correlation measure comprises computing a phase shift to give a correlation value.

4. A method according to claim 1, wherein determining the correlation measure comprises computing frequency spectra of the first and second signals.

5. A method according to claim 1, wherein sensing the electrical signals comprises receiving bipolar electrogram signals.

6. A method according to any of the preceding claims, and comprising interrupting conduction at the site using the probe.

7. A method according to claim 6, wherein sensing the electrical signals comprises sensing respective first and second signals before interrupting the conduction.

8. A method according to claim 6, wherein sensing the electrical signals comprises sensing respective first and second signals after interrupting the conduction.

9. A method according to claim 6, wherein sensing the electrical signals comprises sensing respective first and second pre-interruption signals before interrupting the conduction and sensing respective first and second post-interruption signals after interrupting the conduction, and comprising comparing the correlation measure of the first and second pre-interruption signals with that of the first and second post-interruption signals.

10. A method according to claim 9, wherein comparing the correlation measure comprises:

finding a first correlation measure using the first and second pre-interruption signals;

finding a second correlation measure using the first and second post-interruption signals; and calculating a difference of the first and second correlation measures to determine effectiveness of the treatment.

11. A method according to claim 6, wherein interrupting conduction comprises transferring energy between the probe and the site.

12. A method according to claim 11, wherein transferring energy between the probe and the site comprises ablating the site.

13. A method according to claim 12, wherein ablating the site comprises ablating a generally linear area in the vicinity of the site.

14. A method according to claim 12, wherein ablating the site comprises ablating an area having a complex shape in the vicinity of the site.

15. A method according to claim 11, wherein transferring energy between the probe and the site comprises cooling the site.

16. A method according to claim 15, and comprising determining the effect of cooling the site on the correlation of the signals and ablating the site responsive to the effect.

17. A method for mapping electrical activity in the heart of a subject, comprising:

positioning a probe at a plurality of sites in the heart;

sensing respective first and second electrical signals, using the probe, at first and second points in the endocardium in the respective vicinity of each of the plurality of sites;

processing the signals sensed by the probe to determine a correlation measure of the respective first and second signals at each of the plurality of sites; and producing a map of the correlation measures.

18. A method according to claim 17, wherein producing the map comprises producing a map showing the location of an abnormal conduction path.

19. A method according to claim 17, and comprising the additional steps of:

ablating a lesion at a site in the heart;

positioning the probe in a vicinity of the lesion ablated in the tissue, after producing the map;

receiving electrical signals, using the probe, from at least two points in the vicinity of the lesion after ablation thereof;

processing the signals received by the probe to determine the correlation measure between the signals at the points in the vicinity of the lesion after the ablation; and comparing the measure determined after the ablation to the measure determined before the ablation to determine the effectiveness of treatment.

20. A method for determining the effect of ablation on excitable tissue, comprising:

positioning a probe in a vicinity of a lesion ablated in the tissue;

receiving electrical signals, using the probe, from at least two points in the vicinity; and processing the signals received by the probe to determine a correlation measure between the signals at the points.

21. A method according to claim 20, and comprising comparing the correlation measure with a previous correlation measure determined by processing signals received from at least two of the at least two points before ablating the tissue.

22. A method according to claim 20, wherein receiving signals from the at least two points comprises receiving signals from a plurality of pairs of points, and wherein processing the signals comprises producing a correlation map of the tissue, indicative of the effect of the ablation.

23. A method according to any of claims 17–22, wherein receiving electrogram signals comprises receiving bipolar electrogram signals.

24. A method according to any of claims 17–22, wherein processing the signals to determine the correlation measure comprises performing a time-domain correlation computation.

25. A method according to any of claims 17–22, wherein processing the signals to determine the correlation measure comprises computing a phase shift to give a correlation value.

26. A method according to any of claims 17–22, wherein processing the signals comprises computing frequency spectra of the signals.

27. Intracardiac apparatus, comprising:

an elongate probe for insertion into the heart of a subject, said probe having distal and proximal ends and comprising at least two sensing electrodes near the distal end of the probe, for sensing signals in the heart tissue; and signal analyzer circuitry, which receives the signals from the probe and calculates a correlation measure of the signals.

28. Apparatus according to claim 27, wherein the sensing electrodes comprise bipolar electrodes.

29. Apparatus according to claim 27, wherein the probe comprises a position sensor, which generates signals responsive to the position of the probe with respect to an external frame of reference.

30. Apparatus according to claim 27, wherein the probe is positioned at a plurality of locations in the heart, and the signal analyzer circuitry produces a map of the correlation measures determined at the plurality of locations.

31. Apparatus according to any of claims 27–30, wherein the probe comprises a tissue ablation device adjacent the distal end of the probe.

32. Apparatus according to claim 31, wherein the ablation device comprises an ablation electrode, and wherein one of the at least two sensing electrodes is also an ablation electrode.

33. Apparatus according to claim 31, wherein the ablation device is disposed over and substantially covers the outer surface of the distal end of the probe.

34. Apparatus according to claim 31, wherein the ablation device and electrodes have positions along an outer, radial surface of the probe, wherein one electrode is axially proximal to the ablation device, and the other electrode is axially distal to the ablation device.

35. Apparatus according to claim 31, and comprising a cooler, for cooling the heart tissue, adjacent to the ablation device.

36. Apparatus according to claim 31, and comprising a cooler thermally coupled to the ablation device, which cools the heart tissue.

37. Apparatus for determining the effectiveness of treatment of abnormal conduction in the heart of a subject, comprising:

an elongate probe for insertion into the heart of the heart, said probe having distal and proximal ends and comprising at least two sensing electrodes near the distal end of the probe, for sensing activation signals in the heart tissue; and signal analyzer circuitry, which receives the activation signals from the probe, determines a correlation measure thereof, and compares a first correlation measure determined before the treatment with a second correlation measure determined after the treatment.

38. Apparatus according to claim 37, wherein the sensing electrodes comprise bipolar electrodes.

39. Apparatus according to claim 37, wherein the probe comprises a position sensor near the distal end thereof, which generates signals responsive to the position of the probe with respect to an external frame of reference.

40. Apparatus according to claim 37, wherein the probe is positioned at a plurality of locations in the heart, and the signal analyzer circuitry produces a map of the correlation measures determined at the plurality of locations.

* * * * *